(12) United States Patent
Mikus et al.

(10) Patent No.: US 6,251,105 B1
(45) Date of Patent: *Jun. 26, 2001

(54) CRYOPROBE SYSTEM

(75) Inventors: Paul W. Mikus; Jay J. Eum, both of Irvine, CA (US)

(73) Assignee: Endocare, Inc., Irvine, CA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/052,807

(22) Filed: Mar. 31, 1998

(51) Int. Cl.[7] ..................................... A61B 18/18
(52) U.S. Cl. ................... 606/22; 606/20; 606/23
(58) Field of Search ................ 606/20–26; 62/51.2, 62/293

(56) References Cited

U.S. PATENT DOCUMENTS

| 3,696,813 | 10/1972 | Wallach . | |
|---|---|---|---|
| 3,800,552 | 4/1974 | Sollami et al. | 62/51.2 |
| 3,913,581 | 10/1975 | Ritson et al. . | |
| 4,063,560 | 12/1977 | Thomas et al. . | |
| 4,275,734 | 6/1981 | Mitchiner . | |
| 4,278,090 | 7/1981 | Van Gerven . | |
| 5,098,428 | * 3/1992 | Sandlin et al. | 606/20 |
| 5,388,415 | 2/1995 | Glinka et al. | 62/51.2 |
| 5,452,582 | 9/1995 | Longsworth | 62/51.2 |
| 5,522,870 | 6/1996 | Ben-Zion | 607/104 |

FOREIGN PATENT DOCUMENTS 1217377    3/1986   (SU) .............................. A61B/17/36

OTHER PUBLICATIONS

Walker, Miniature Refrigerators for Cryogenic Sensor and Cold Electronics (1989) (Chapter 2).
Onik, Ultrasound–Guided Cryosurgery, Scientific American at 62 (Jan. 1996).
Onik, Cohen, et al., Transrectal Ultrasound–Guided Percutaneous Radical Cryosurgical Ablation of the Prostate, 72 Cancer 1291 (1993).
Walker & Gingham, Low Capacity Cryogenic Refrigeration, pp. 67 et seq (1994).

* cited by examiner

Primary Examiner—Linda C. M. Dvorak
Assistant Examiner—R. Kearney
(74) Attorney, Agent, or Firm—K. David Crockett, Esq.; Crockett & Crockett

(57) ABSTRACT

A cryoprobe system with a vented high pressure gas supply line. Venting of the gas supply line upon cut-off of high pressure gas quickens the warming process of the cryoprobe.

12 Claims, 2 Drawing Sheets

CRYOPROBE SYSTEM

FIELD OF THE INVENTION

This invention relates to cryocoolers, and to cryoprobes for use in cryosurgery.

BACKGROUND OF THE INVENTION

Cryosurgical probes are used to treat a variety of diseases. The cryosurgical probes quickly freeze diseased body tissue, causing the tissue to die, after which it will be absorbed by the body or expelled by the body or sloughed off. Cryothermal treatment is currently used to treat prostate cancer and benign prostate disease, breast tumors and breast cancer, liver tumors and cancer, glaucoma and other eye diseases. Cryosurgery is also proposed for the treatment of a number of other diseases.

The use of cryosurgical probes for cryoablation of prostate is described in Onik, *Ultrasound-Guided Cryosurgery, Scientific American* at 62 (Jan. 1996) and Onik, Cohen, et al., *Transrectal Ultrasound-Guided Percutaneous Radial Cryosurgical Ablation Of The Prostate,* 72 Cancer 1291 (1993). In this procedure, generally referred to as cryoablation of the prostate, several cryosurgical probes are inserted through the skin in the perineal area (between the scrotum and the anus) which provides the easiest access to the prostate. The probes are pushed into the prostate gland through previously place cannulas. Placement of the probes within the prostate gland is visualized with an ultrasound imaging probe placed in the rectum. The probes are quickly cooled to temperatures typically below −120° C. The prostate tissue is killed by the freezing, and any tumor or cancer within the prostate is also killed. The body will absorb some of the dead tissue over a period of several weeks. Other necrosed tissue may slough off through the urethra. The urethra, bladder neck sphincter and external sphincter are protected from freezing by a warming catheter placed in the urethra and continuously flushed with warm saline to keep the urethra from freezing.

Rapid re-warming of cryosurgical probes is desired. Cryosurgical probes are warmed to promote rapid thawing of the prostate, and upon thawing the prostate is frozen once again in a second cooling cycle. The probes cannot be removed from frozen tissue because the frozen tissue adheres to the probe. Forcible removal of a probe which is frozen to surrounding body tissue leads to extensive trauma. Thus many cryosurgical probes provide mechanisms for warming the cryosurgical probe with gas flow, condensation, electrical heating, etc.

A variety of cryosurgical instruments, variously referred to as cryoprobes, cryosurgical ablation devices, and cryostats and cryocoolers, have been available for cryosurgery. The preferred device uses Joule-Thomson cooling in devices known as Joule-Thomson cryostats. These devices take advantage of the fact that most gases, when rapidly expanded, become extremely cold. In these devices, a high pressure gas such as argon or nitrogen is expanded through a nozzle inside a small cylindrical sheath made of steel, and the Joule-Thomson expansion cools the steel sheath to sub-freezing cryogenic temperature very rapidly.

An exemplary device is illustrated in Sollami, Cryogenic Surgical Instrument, U.S. Pat. No. 3,800,552 (Apr. 2, 1974). Sollami shows a basic Joule-Thomson probe with a sheath made of metal, a fin-tube helical gas supply line leading into a Joule-Thomson nozzle which directs expanding gas into the probe. Expanded gas is exhausted over the fin-tube helical gas supply line, and pre-cools incoming high pressure gas. For this reason, the coiled supply line is referred to as a heat exchanger, and is beneficial because, by pre-cooling incoming gas, it allows the probe to obtain lower temperatures.

Ben-Zion, Fast Changing Heating and Cooling Device and Method, U.S. Pat. No. 5,522,870 (Jun. 4, 1996) applies the general concepts of Joule-Thomson devices to a device which is used first to freeze tissue and then to thaw the tissue with a heating cycle. Nitrogen is supplied to a Joule-Thomson nozzle for the cooling cycle, and helium is supplied to the same Joule-Thomson nozzle for the warming cycle. Preheating of the helium is presented as an essential part of the invention, necessary to provide warming to a sufficiently high temperature. Essentially the same system, using helium gas to warm a cryosurgical probe, injected into the cryosurgical probe through the same supply line and Joule-Thomson nozzle used for cooling was clearly illustrated in 1986 by Soviet scientists E. N. Murinets-Markevich, et al. in Soviet Patent SU 1,217,377. Our own U.S. patent app. Ser. No. 08/685,233 (filed Jul. 23, 1996), also uses Joule-Thomson warming in a system which provides for control of the freeze zone at the tip of the cryoprobe.

A Joule-Thomson cryostat for use as a gas tester is illustrated in Glinka, System for a Cooler and Gas Purity Tester, U.S. Pat. No. 5,388,415 (Feb. 14, 1995). Glinka also discloses use of a by-pass from the Joule-Thomson Nozzle to allow for cleaning the supply line, and also mentions that the high flow of gas in the by-pass mode will warm the probe. This is referred to as mass flow warming, because the warming effect is accomplished purely by conduction and convection of heat from the fluid mass flowing through the probe.

Various cryocoolers use mass flow warming, flushed backwards through the probe, to warm the probe after a cooling cycle. Lamb, Refrigerated Surgical Probe, U.S. Pat. No. 3,913,581 (Aug. 27, 1968) is one such probe, and includes a supply line for high pressure gas to a Joule-Thomson expansion nozzle and a second supply line for the same gas to be supplied without passing through a Joule-Thomson nozzle, thus warming the catheter with mass flow. Longsworth, Cryoprobe, U.S. Pat. No. 5,452,582 (Sep. 26, 1995) discloses a cryoprobe which uses the typical fin-tube helical coil heat exchanger in the high pressure gas supply line to the Joule-Thomson nozzle. The Longsworth cryoprobe has a second inlet in the probe for a warming fluid, and accomplishes warming with mass flow of gas supplied at about 100 psi. The heat exchanger, capillary tube and second inlet tube appear to be identical to the cryostats previously sold by Carleton Technologies, Inc. of Orchard Park, N.Y.

Still other Joule-Thomson cryocoolers use the mechanism of flow blocking to warm the cryocooler. In these systems, the high pressure flow of gas is stopped by blocking the cryoprobe outlet, leading to the equalization of pressure within the probe and eventual stoppage of the Joule-Thomson effect. Examples of these systems include Wallach, Cryosurgical Apparatus, U.S. Pat. No. 3,696,813 (Oct. 10, 1973). These systems reportedly provide for very slow warming, taking 10–30 seconds to warm sufficiently to release frozen tissue attached to the cold probe. Thomas, et al., Cryosurgical Instrument, U.S. Pat. No. 4,063,560 (Dec. 20, 1977) provides an enhancement to flow blocking, in which the exhaust flow is not only blocked, but is reversed by pressurizing the exhaust line with high pressure cooling gas, leading to mass buildup and condensation within the probe.

Each of the above mentioned cryosurgical probes builds upon prior art which clearly establishes the use of Joule- Thomson cryocoolers, heat exchangers, thermocouples, and other elements of cryocoolers. Walker, *Miniature Refrigerators for Cryogenic Sensor and Cold Electronics* (1989) (Chapter 2) and Walker & Gingham, Low *Capacity Cryogenic Refrigeration*, pp. 67 et seq. (1994) show the basic construction of Joule-Thomson cryocoolers including all of these elements. The Giaque-Hampson heat exchanger, characterized by coiled finned-tube, transverse flow recuperative heat exchanger is typical of cryocoolers. The open mandrel around which the finned tube coil is placed is also typical of cryocoolers.

Each of the warming mechanisms of the prior art may be classified as mass flow warming (Glinka), reverse mass flow warming (Longsworth), Joule-Thomson warming (Murinets-Markevich, Ben Zion, and Mikus), or flow blocking (Wallach). In all of these systems, flow of cooling gas is supplied through a long high pressure line, usually several feet (one or two meters) of tubing to connect the cryoprobe with the gas supply manifold. When flow of cooling gas is cut off, there is a substantial volume of high pressure cooling gas in the supply line. This gas has only one place to go: through the cryoprobe, and Joule-Thomson nozzle, then out of the downstream exhaust line leading from the cryoprobe. It takes several seconds for the pressure to dissipate through the probe, and during this dissipation the Joule-Thomson effect continues and the probe continues cooling. This situation delays the desired warming of the cryoprobe and limits the control that a surgeon may exercise over the cooling and warming of tissue.

SUMMARY

The system described below provides for more immediate stoppage of the Joule-Thomson cooling effect than is possible with mere cooling gas cut-off. The system includes a vent for the cooling gas supply line. To stop the cooling effect, the supply of cooling gas is cut off and this vent is opened. The reservoir of high pressure gas in the supply line is thereby vented into the operating room, and therefor does not dissipate through the Joule-Thomson nozzle. Cooling of the probe is immediately stopped, and warming commences as soon as the system is aligned in the warming mode.

DETAILED DESCRIPTION OF THE INVENTION

Figure 1:
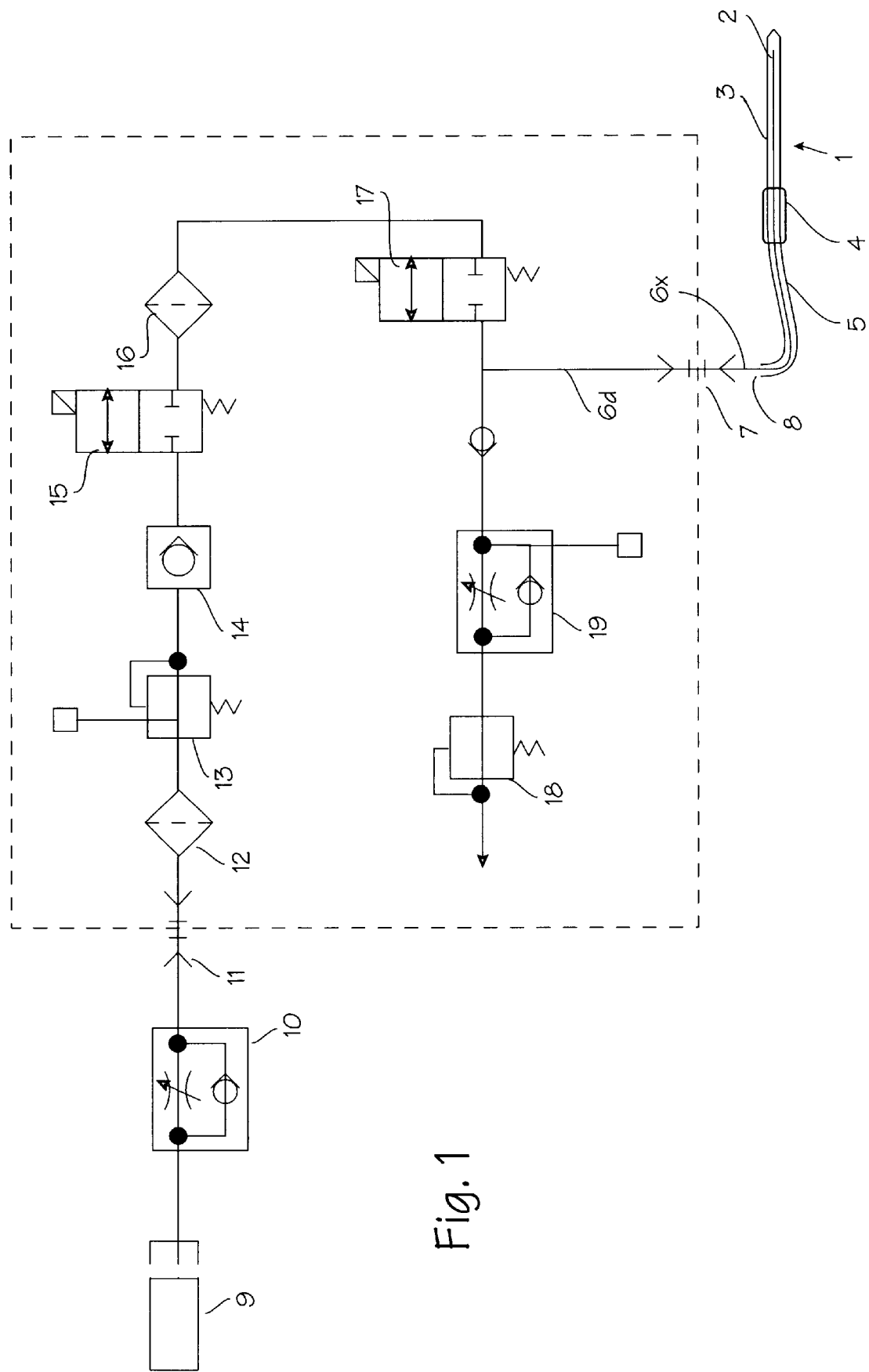
FIG. 1 is a schematic view of the supply system for a Joule-Thomson cryoprobe incorporating a vented gas supply line.

FIG. 1 is a schematic view of the supply system for a Joule-Thomson cryoprobe incorporating a vented gas supply line. The system supplies a cryoprobe 1 which may be any one of the many cryoprobes used for various forms of cryosurgery. The probe has a Joule-Thomson nozzle 2 inside a probe outer sheath 3, and a handle 4 of convenient size. The flexible tube 5 houses gas supply line 6 which supplies high pressure cooling gas, usually nitrogen or argon, to the cryoprobe. The gas supply line is connected to a high pressure gas supply through high pressure fitting 7. The cryoprobe has an exhaust gas pathway inside the flexible tube, which takes cold expanded gas from the cryoprobe to exhaust port 8 at the proximal end of the flexible tube. The exhaust port may be located near or at the high pressure fitting.

The gas supply system starts with the tank 9 of cooling gas. The cooling gas is typically argon or nitrogen, and is typically stored at about 6000 psi. The cooling gas supply line routes cooling gas through the external pressure regulator 10, which regulates pressure in the line to 3200 psi for supply to the system. The cooling gas supply line continues into the manifold through high pressure fitting 11. The supply line inside the manifold is provided with a filter 12, and internal pressure regulator 13 set at 3000 psi, and relief valve 14, a high pressure supply valve 15, a moisture filter 16, and a second high pressure valve 17 used as the operating cutoff valve. From the high pressure valve 17, the downstream portion of the high pressure supply line 6, designated as item 6d, is aligned to the cryoprobe through high pressure fitting 7. The system described thus far serves to supply high pressure cooling gas to the cryoprobe. The external portion 6x of the high pressure supply line is typically several feet long (one or two meters), and this length of tubing creates a reservoir of high pressure gas that is responsible for delay in system response when the operating cut-off valve 17 is closed. Although the operator of the system has intended to stop the cooling operation of the cryoprobe, cooling will continue until the reservoir of high pressure gas in line 6d and 6x forces itself through the Joule-Thomson nozzle in the probe and pressure in the line is dissipated out the exhaust 8.

The vent used to clear the high pressure cooling gas supply line is connected to the line 6d within the manifold and downstream of the operating cut-off valve 17. The vent comprises a solenoid operated valve 18 and a pressure regulator 19. The solenoid operated valve 18 acts as the vent when opened, providing an alternate path for the high pressure gas in supply line portions 6d and 6x to escape (rather than passing through the probe and expanding through the Joule-Thomson nozzle). This eliminates essentially all delay between operator commands to the system to cease cooling and actual cessation of cooling. The pressure regulator, set nominally at 150 pounds, reduces the noise of the discharge through the valve 18.

In use, the cryoprobe is inserted into the body or placed in contact with the body, depending on the operation to be performed. When the cryoprobe is properly located and cooling is desired, the operator (usually a highly trained surgeon) operates the system to initiate flow of high pressure cooling gas to the cryoprobe. The first high pressure supply valve 15 is opened to supply the system with high pressure gas, and is typically left open during the entire cryosurgical procedure. The second high pressure valve, referred to here as the operating cut-off valve 17, is opened and closed in response to commands from the operator to initiate cooling. The commands may be manual switch operations which provide for direct operator control of the solenoid which operates the valve, or the commands may be provided through software in response to operator input through a key board, a touch pad or push buttons or any other convenient operator interface. When the operator closes operating cut-off valve 17, the valve 18 opens automatically to vent high pressure gas from the supply line portions 6d and 6x. The automatic operation of vent valve 18 may be accomplished through electro-mechanical interlocks between operating cut-off valve 17 and vent valve 18, or mechanical interlocks (the two valves may be combined into a single three way valve), or they may be accomplished through software used to control the system. It should be appreciated that quick operation of vent valve 18, immediately upon closure or operating cut-off valve 17 or even simultaneous with closure or operating cut-off valve 17, is preferred. The vent valve 18 automatically closes when the pressure in the high pressure gas supply line reaches some pre-set low pressure (the pre-set pressure may be atmospheric pressure). With the vent valve closed, the system is ready for another cooling operation.

The low pressure regulator 19 shown in FIG. 1 lowers the vented gas pressure before release from the system, thereby reducing the noise caused by the venting process. This regulator may be omitted in environments where the noise of venting 3000 psi gas (a very loud honk) can be tolerated. A muffler may be used at the vent gas outlet 20 to further reduce vent noise.

The vent system is described in relation to the single probe shown in FIG. 1. This system is also intended for use in a cryosurgical system which includes several cryosurgical probes. The system may also include a gas supply line for warming gas supply to the Joule Thomson nozzle. The vent system may be applied to each cryoprobe in the system, and may be applied to the warming gas supply line in those systems using Joule-Thomson warming in order to avoid delay in the cessation of warming.

Figure 2:
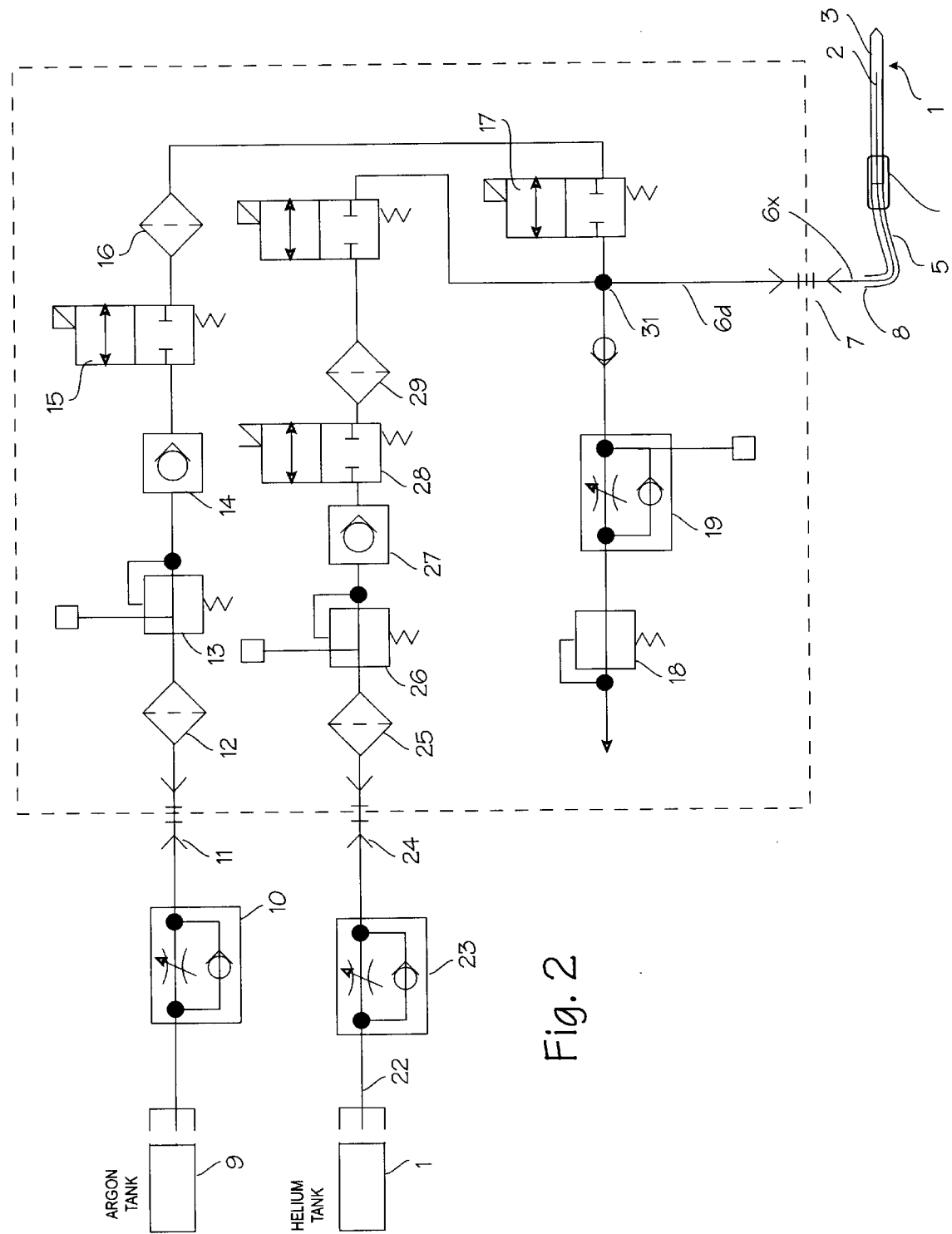
FIG. 2 is a schematic view of the supply system for a Joule-Thomson cryoprobe incorporating a vented gas supply line in a Joule-Thomson warming system.

For application to the warming portion of system is illustrated in FIG. 2. The gas supply system starts with the tank 21 of warming gas. The warming gas is typically helium or hydrogen, and is typically stored at about 6000 psi. The warming gas supply line 22 routes warming gas through the external pressure regulator 23, which regulates pressure in the line to 3200 psi for supply to the system. The warming gas supply line continues into the manifold through high pressure fitting 24. The supply line inside the manifold is provided with a filter 25, and internal pressure regulator 26 set at 3000 psi, and relief valve 27, a high pressure supply valve 28, a moisture filter 29, and a second high pressure valve 30 used as the operating cutoff valve. From the high pressure valve 30, the downstream portion of the high pressure supply line 22, designated as item 22d, is aligned to the cryoprobe through junction 31 with the downstream portion of the high pressure supply line 6d, and subsequently through high pressure fitting 7. Just as in the cooling mode, the external portion 6x of the high pressure supply line is typically several feet long (one or two meters), and this length of tubing creates a reservoir of high pressure gas that is responsible for delay in system response when the operating cut-off valve 30 is closed. Although the operator of the system has intended to stop the warming operation of the cryoprobe, warming will continue until the reservoir of high pressure gas in line 6d and 6x forces itself through the Joule-Thomson nozzle in the probe and pressure in the line is dissipated. The operation of the solenoid operated valve 18 serves to vent the warming gas and cease warming flow in the same manner as described above in relation to cessation of cooling flow.

The vent system has been described in relation to a cryosurgical system in order to highlight its usefulness, but it may be also used in various cryogenic systems requiring rapid cessation of cooling flow. The industrial applications contemplated in Ben-Zion, U.S. Pat. No. 5,522,870, including material treatment and surface curing, may be improved with the vented system described above. Thus, while the preferred embodiments of the devices and methods have been described in reference to the environment in which they were developed, they are merely illustrative of the principles of the inventions. Other embodiments and configurations may be devised without departing from the spirit of the inventions and the scope of the appended claims.

What is claimed is:

1. A cryosurgical system comprising:
   a Joule-Thomson cryoprobe;
   a high pressure gas supply line aligned to supply gas to the Joule-Thomson cryoprobe;
   an operating cut-off valve operatively connected to the high pressure gas supply line, said valve being operable to supply and cut off high pressure gas to the Joule-Thomson cryoprobe;
   a vent valve operatively connected to the high pressure gas supply line, said valve being operable to vent gas from the high pressure supply line immediately upon operation of the operating cut-off valve to cut off high pressure gas to the Joule-Thomson cryoprobe; and
   an interlock for controlling the vent valve, said interlock operable to open the vent valve immediately upon operation of the cut-off valve to cut off high pressure gas to the Joule-Thomson cryoprobe.

2. The system of claim 1 wherein the interlock is a software controlled interlock.

3. The system of claim 1 wherein the interlock is an electrical interlock.

4. The system of claim 1 wherein the interlock is a mechanical interlock.

5. A cryosurgical system for use in a body of a patient, said system comprising:
   a cryoprobe comprising a closed end tube adapted for insertion into the body of the patient and a Joule-Thomson nozzle housed within the tube;
   a high pressure gas supply line aligned to supply gas to the Joule-Thomson nozzle;
   an operating cut-off valve operatively connected to the high pressure gas supply line, said valve being operable to supply and cut off high pressure gas to the Joule-Thomson nozzle;
   a vent valve operatively connected to the high pressure gas supply line, said valve being operable to vent gas from the high pressure supply line immediately upon operation of the operating cut-off valve to cut off high pressure gas to the Joule-Thomson nozzle; and
   an interlock for controlling the vent valve, said interlock operable to open the vent valve immediately upon operation of the cut-off valve to cut off high pressure gas to the cryoprobe.

6. The system of claim 5 wherein the interlock is a software controlled interlock.

7. The system of claim 5 wherein the interlock is an electrical interlock.

8. The system of claim 5 wherein the interlock is a mechanical interlock.

9. A cryosurgical system for use in a body of a patient, said system comprising:
   a cryoprobe comprising a closed end tube adapted for insertion into the body of the patient and a Joule-Thomson nozzle housed within the tube;
   a high pressure gas supply line aligned to supply gas to the Joule-Thomson nozzle;
   an exhaust gas pathway aligned with the closed end tube for exhausting gas from the tube after the gas has passed through the Joule-Thomson nozzle;
   an operating cut-off valve in the high pressure gas supply line, said valve being operable to supply and cut off high pressure gas to the Joule-Thomson nozzle;
   a vent valve in the high pressure gas supply line, said valve being operable to vent gas from the high pressure supply line to atmospheric pressure immediately upon operation of the operating cut-off valve to cut off high pressure gas to the Joule-Thomson nozzle; and an interlock for controlling the vent valve, said interlock operable to open the vent valve immediately upon operation of the cut-off valve to cut off high pressure gas to the cryoprobe.

10. The system of claim 9 wherein the interlock is a software controlled interlock.

11. The system of claim 9 wherein the interlock is an electrical interlock.

12. The system of claim 9 wherein the interlock is a mechanical interlock.

* * * * *